US012778907B2

(12) United States Patent
Li et al.

(10) Patent No.: US 12,778,907 B2
(45) Date of Patent: Nov. 3, 2026

(54) USE OF MITOXANTRONE HYDROCHLORIDE LIPOSOME

(71) Applicant: CSPC ZHONGQI PHARMACEUTICAL TECHNOLOGY (SHIJIAZHUANG) CO., LTD, Shijiazhuang (CN)

(72) Inventors: Chunlei Li, Shijiazhuang (CN); Yanping Liu, Shijiazhuang (CN); Caixia Wang, Shijiazhuang (CN); Yanling Du, Shijiazhuang (CN); Xiaoyan Wang, Shijiazhuang (CN); Xueying Shen, Shijiazhuang (CN); Shixia Wang, Shijiazhuang (CN); Shanshan Sun, Shijiazhuang (CN)

(73) Assignee: CSPC ZHONGQI PHARMACEUTICAL TECHNOLOGY (SHIJIAZHUANG) CO., LTD, Shijiazhuang (CN)

( * ) Notice: Subject to any disclaimer, the term of this patent is extended or adjusted under 35 U.S.C. 154(b) by 563 days.

(21) Appl. No.: 18/266,870

(22) PCT Filed: Dec. 14, 2021

(86) PCT No.: PCT/CN2021/137728

§ 371 (c)(1),
(2) Date: Jun. 13, 2023

(87) PCT Pub. No.: WO2022/127760

PCT Pub. Date: Jun. 23, 2022

(65) Prior Publication Data

US 2024/0058280 A1 Feb. 22, 2024

(30) Foreign Application Priority Data

Dec. 15, 2020 (CN) ........................ 202011477966.6

(51) Int. Cl.

| | |
|---|---|
| ***A61K 31/136*** | (2006.01) |
| ***A61K 9/1271*** | (2025.01) |
| ***A61P 35/00*** | (2006.01) |

(52) U.S. Cl.

CPC .......... *A61K 31/136* (2013.01); *A61K 9/1271* (2013.01); *A61P 35/00* (2018.01)

(58) Field of Classification Search

CPC .... A61K 31/136; A61K 9/1271; A61K 9/127; A61P 35/00

See application file for complete search history.

(56) References Cited

U.S. PATENT DOCUMENTS

| | | | | |
|---|---|---|---|---|
| 10,028,913 | B2 | 7/2018 | Li et al. | |
| 10,421,754 | B2 | 9/2019 | Shi et al. | |
| 11,033,520 | B2 | 6/2021 | Nikoulin et al. | |
| 11,583,508 | B2 | 2/2023 | Li et al. | |
| 2003/0219476 | A1* | 11/2003 | Ahmad ................... | A61P 25/00 514/649 |
| 2011/0002977 | A1* | 1/2011 | Li ........................ | A61K 9/1273 514/285 |
| 2024/0269092 | A1 | 8/2024 | Li et al. | |

FOREIGN PATENT DOCUMENTS

| | | | | |
|---|---|---|---|---|
| CN | 1469735 | A | 1/2004 | |
| CN | 1242740 | C | 2/2006 | |
| CN | 101176710 | A | 5/2008 | |
| CN | 101209243 | A | 7/2008 | |
| CN | 100539997 | C | 9/2009 | |
| CN | 102397561 | A | 4/2012 | |
| CN | 103622909 | A | 3/2014 | |
| CN | 104971044 | A | 10/2015 | |
| CN | 105287383 | A | 2/2016 | |
| CN | 105748449 | A | 7/2016 | |
| CN | 109718228 | A | 5/2019 | |
| CN | 112043832 | A * | 12/2020 | ......... A61K 31/4709 |
| JP | 2006-515578 | A | 6/2006 | |
| JP | 2019-533006 | A | 11/2019 | |
| WO | 2004/047800 | A2 | 6/2004 | |
| WO | WO 2008/080367 | A1 | 7/2008 | |
| WO | WO 2016/023330 | A1 | 2/2016 | |
| WO | 2020/011189 | A1 | 1/2020 | |
| WO | WO 2022/247921 | A1 | 12/2022 | |

OTHER PUBLICATIONS

English machine translation of CN-112043832-A made Jun. 17, 2026. (Year: 2026).*

Nicoletto et al., "Pharmacokinetics of intraperitoneal hyperthermic perfusion with mitoxantrone in ovarian cancer", 2000, Cancer Chemotherapy and Pharmacology, vol. 45, pp. 457-462. (Year: 2000).*

Australian Patent Office, Examination Report No. 1 issued in counterpart Australian Patent Application No. 2021399438, mailed on May 9, 2024.

He et al., "Design of multifunctional magnetic iron oxide nanoparticles/mitoxantrone-loaded liposomes for both magnetic resonance imaging and targeted cancer therapy", *International Journal of Nanomedicine*, 9: 4055-4066 (2014).

Dugan et al., "Multicenter Phase II Trial of Mitoxantrone in Patients With Advanced Nasopharyngeal Carcinoma in Southeast Asia: An Asian-Oceanian Clinical Oncology Association Group Study", Journal of Clinical Oncology, 11(1): 70-76 (1993).

Tila et al., "pH-Sensitive, Polymer Modified, Plasma Stable Niosomes: Promising Carriers for Anti-Cancer Drugs", EXCLI Journal, 14: 21-32 (2015).

(Continued)

*Primary Examiner* — Michael B. Pallay

(74) *Attorney, Agent, or Firm* — Leydig, Voit & Mayer, Ltd.

(57) ABSTRACT

The present application provides a use of mitoxantrone hydrochloride liposome in the preparation of a medicament for treating ovarian cancer, gastric cancer or head and neck squamous cell carcinoma, a method for treating ovarian cancer, gastric cancer or head and neck squamous cell carcinoma using a mitoxantrone hydrochloride liposome formulation, and a mitoxantrone hydrochloride liposome formulation for treating ovarian cancer, gastric cancer or head and neck squamous cell carcinoma.

17 Claims, No Drawings

(56) References Cited

OTHER PUBLICATIONS

Wang et al., "Mitoxantrone hydrochloride (MTX) induces apoptosis of human nasopharyngeal carcinoma cell line CNE—2 via PI3K pathway", Modern Oncology, 23(2): 0153-0156 (2015) (English abstract only).
Xu et al. (Ed.), "New, Comprehensive, and Practical Manual of Drug" (4th Ed.), 4 pages (2018), English translation included.
Yang et al., "Phase I clinical trial of pegylated liposomal mitoxantrone plm60-s: pharmacokinetics, toxicity and preliminary efficacy", Cancer Chemother Pharmacol, 74:637-646 (2014).
China National Intellectual Property Administration, International Search Report and Written Opinion issued in International Patent Application No. PCT/CN2021/137728, mailed on Feb. 16, 2022.
Markman et al., "Salvage Intraperitoneal Mitoxantrone Therapy of Ovarian Cancer: Influence of Increasing the Volume of Treatment", Gynecologic Oncology, 49:185-189 (1993).

* cited by examiner

USE OF MITOXANTRONE HYDROCHLORIDE LIPOSOME

CROSS-REFERENCE TO RELATED APPLICATIONS

The present application is the U.S. National Stage of International Patent Application No. PCT/CN2021/137728, filed Dec. 14, 2021, which claims priority to Chinese Patent Application No. 202011477966.6, filed on Dec. 15, 2020, each of which is hereby incorporated by reference in its entirety for all purposes.

TECHNICAL FIELD

The present application generally relates to the field of medicine, and in particular to use of mitoxantrone hydrochloride liposome in the treatment of ovarian cancer, gastric cancer or head and neck squamous cell carcinoma.

BACKGROUND OF THE INVENTION

Ovarian cancer is one of the common malignancies in women. Due to lack of typical symptoms and signs, ovarian cancer, once diagnosed, is mostly in the middle or late stage and patients have very short survival periods. Ovarian cancer has many pathological types, and the most common type is epithelial ovarian cancer, accounting for 70% of cases, followed by malignant germ cell tumors and sex cord stromal tumors.

The overall prognosis of ovarian epithelial carcinoma is poor due to difficulty in early diagnosis and lack of effective treatment for drug-resistant recurrent ovarian epithelial carcinoma. Surgery plus chemotherapy is the main therapeutic regimen for ovarian malignancies. Chemotherapy plays an important role in adjuvant treatment and relapse treatment. Platinum-based combination chemotherapy is the main recommended regimen for postoperative chemotherapy for advanced ovarian cancer. 70% to 80% of advanced patients relapse even if complete remission is achieved by the above treatment. Currently, the initial standard chemotherapy regimen for advanced epithelial ovarian cancer is platinum-based combined chemotherapy. The choice of specific regimens should take into account the personal characteristics of patients. Other recommended regimens include carboplatin plus anthracycline doxorubicin liposome. In addition, doxorubicin liposome is recommended to be used alone or in combination with bevacizumab for the treatment of recurrent drug-resistant ovarian cancer. However, among all current monotherapies for the recurrent platinum-resistant ovarian cancer, no one is better than the others in terms of safety and efficacy.

Gastric cancer is the fifth most prevalent cancer in the world. For patients who cannot receive radical cures by surgery or have metastatic gastric cancer, it is currently accepted that comprehensive therapies based on systemic drug therapies should be adopted. Commonly used systemic chemotherapeutic drugs include 5-fluorouracil (5-FU), capecitabine, tigio, cisplatin, oxaliplatin, paclitaxel, docetaxel, albumin paclitaxel, irinotecan, and epirubicin. Targeted therapeutic drugs include trastuzumab and apatinib. The treatment of advanced recurrent/metastatic gastric cancer is difficult, particularly with poor efficacy and limited choice of second-line and third-line therapies.

The incidence rates of head and neck tumors rank sixth in the world, including tumors originating in a nasal cavity, sinus, nasopharynx, oropharynx, laryngopharynx, cervical esophagus, thyroid, salivary gland, oral cavity, larynx, and ear. 90% of head and neck tumors are head and neck squamous carcinomas (SCCHN), with more than 550,000 new cases and more than 300,000 deaths per year worldwide. Most patients cannot be cured due to local recurrence and metastasis. The five-year survival rate is less than 50%. Surgery and chemoradiotherapy do not achieve satisfactory treatment outcomes.

For patients with recurrent head and neck tumors, only a small proportion of them can be re-treated with radical local therapies such as surgery or radiotherapy, and most of them, like patients having metastasis, receive either palliative systemic therapy (PS 0-1) or optimal supportive care (PS≥2). Cisplatin in combination with 5-FU (PF regimen) or in combination with paclitaxel is a common option in first-line chemotherapeutic regimens. Cisplatin can be replaced with carboplatin if the patient is unsuitable for cisplatin. All above regimens can further include cetuximab.

For recurrent and metastatic head and neck squamous cell carcinoma that has undergone a first-line platinum-based therapy failure, there is not a standard treatment regimen currently. Commonly used drugs are methotrexate, paclitaxel, docetaxel, cetuximab, or immune checkpoint inhibitors. For patients who have undergone first-line platinum-based therapy failures and need second-line/salvage therapies, immunotherapy drugs or other regimens may be selected based on PD-L1 test results.

Thus, for refractory cancer like ovarian cancer, gastric cancer, or head and neck squamous carcinoma, there is an urgent need for better therapeutic products and regimens.

BRIEF SUMMARY OF THE INVENTION

In a first aspect, the present application provides use of mitoxantrone hydrochloride liposome in the manufacture of a medicament for the treatment of ovarian cancer, gastric cancer or head and neck squamous cell carcinoma.

In some embodiments, mitoxantrone hydrochloride liposome is the only active ingredient in the medicament.

In some embodiments, the medicament or mitoxantrone hydrochloride liposome has one or more of the following properties:

(i) the mitoxantrone hydrochloride liposome having a particle size of about 30 to 80 nm, such as about 35 to 75 nm, about 40 to 70 nm, about 40 to 60 nm, or about 60 nm;

(ii) the mitoxantrone hydrochloride interacting with a multivalent counter ion (e.g., sulfate, citrate or phosphate) in the liposome to form a poorly soluble precipitate;

(iii) a phospholipid bilayer in the mitoxantrone hydrochloride liposome containing a phospholipid having a phase transition temperature (Tm) higher than body temperature, such that the liposome has a phase transition temperature higher than body temperature, for example, the phospholipid being selected from the group consisting of hydrogenated soy phosphatidylcholine, phosphatidylcholine, hydrogenated egg yolk lecithin, dipalmitate lecithin, distearate lecithin, or any combination thereof, (iv) a phospholipid bilayer in mitoxantrone hydrochloride liposome containing hydrogenated soy phosphatidylcholine, cholesterol and PEG2000 modified distearoylphosphatidylethanolamine (DSPE-PEG2000).

In some embodiments, a phospholipid bilayer in the mitoxantrone hydrochloride liposome contains hydrogenated soy phosphatidylcholine, cholesterol and PEG2000 modified distearoylphosphatidylethanolamine in a mass ratio of about 3:1:1, the mitoxantrone hydrochloride interacts with a multivalent acid ion in the liposome to form a poorly soluble precipitate, and the mitoxantrone hydrochloride liposome has a particle size of about 60 nm in the medicament.

In some embodiments, the ovarian cancer is platinum-refractory or platinum-resistant recurrent ovarian cancer.

In some embodiments, the gastric cancer is advanced gastric cancer.

In some embodiments, the head and neck squamous cell carcinoma is a squamous cell carcinoma occurring in a nasal cavity, sinus, nasopharynx, oropharynx, laryngopharynx, cervical esophagus, thyroid, salivary gland, oral cavity, larynx and/or ear.

In some embodiments, the head and neck squamous cell carcinoma is recurrent or metastatic head and neck squamous cell carcinoma that has undergone a first-line therapy failure, for example, the first-line therapy is a combination therapy of cisplatin or carboplatin and 5-FU or paclitaxel, optionally further in combination with cetuximab.

In some embodiments, the medicament is in the form of an injection, such as a liquid injection, a powder for injection, or a tablet for injection.

In some embodiments, the medicament is a liquid injection.

In some embodiments, the active ingredient content of the medicament is 0.5 to 5 mg/ml, e.g., 1 to 2 mg/ml or 1 mg/ml, on the basis of mitoxantrone.

In a second aspect, the application provides a method of treating ovarian cancer, gastric cancer, or head and neck squamous carcinoma in a subject, comprising administering to the subject a pharmaceutical composition comprising a therapeutically effective amount of mitoxantrone hydrochloride liposome.

In some embodiments, mitoxantrone hydrochloride liposome is the only active ingredient in the pharmaceutical composition.

In some embodiments, the pharmaceutical composition or the mitoxantrone hydrochloride liposome has one or more of the following properties:

(i) the mitoxantrone hydrochloride liposome having a particle size of about 30 to 80 nm, such as about 35 to 75 nm, about 40 to 70 nm, about 40 to 60 nm, or about 60 nm;

(ii) the mitoxantrone hydrochloride interacting with a multivalent counter ion (e.g., sulfate, citrate or phosphate) in the liposome to form a poorly soluble precipitate;

(iii) a phospholipid bilayer in the mitoxantrone hydrochloride liposome containing a phospholipid having a phase transition temperature (Tm) higher than body temperature, such that the liposome has a phase transition temperature higher than body temperature, for example, the phospholipid being selected from the group consisting of hydrogenated soy phosphatidylcholine, phosphatidylcholine, hydrogenated egg yolk lecithin, dipalmitate lecithin, distearate lecithin, or any combination thereof, (iv) a phospholipid bilayer in mitoxantrone hydrochloride liposome containing hydrogenated soy phosphatidylcholine, cholesterol and PEG2000 modified distearoylphosphatidylethanolamine (DSPE-PEG2000).

In some embodiments, a phospholipid bilayer in the mitoxantrone hydrochloride liposome contains hydrogenated soy phosphatidylcholine, cholesterol and PEG2000 modified distearoylphosphatidylethanolamine in a mass ratio of about 3:1:1, the mitoxantrone hydrochloride interacts with a multivalent acid ion in the liposome to form a poorly soluble precipitate, and the mitoxantrone hydrochloride liposome has a particle size of about 60 nm in the medicament.

In some embodiments, the ovarian cancer is platinum-refractory or platinum-resistant recurrent ovarian cancer.

In some embodiments, the gastric cancer is advanced gastric cancer.

In some embodiments, the head and neck squamous cell carcinoma is a squamous cell carcinoma occurring in a nasal cavity, sinus, nasopharynx, oropharynx, laryngopharynx, cervical esophagus, thyroid, salivary gland, oral cavity, larynx and/or ear.

In some embodiments, the head and neck squamous cell carcinoma is recurrent or metastatic head and neck squamous cell carcinoma that has undergone a first line therapy failure, for example, the first line therapy is a combination therapy of cisplatin or carboplatin and 5-FU or paclitaxel, optionally further in combination with cetuximab.

In some embodiments, the pharmaceutical composition is in the form of an injection, such as a liquid injection, a powder for injection, or a tablet for injection.

In some embodiments, the pharmaceutical composition is a liquid injection.

In some embodiments, the active ingredient content of the pharmaceutical composition is 0.5 to 5 mg/ml, e.g., 1 to 2 mg/ml or 1 mg/ml, on the basis of mitoxantrone.

In some embodiments, the pharmaceutical composition is administered by intravenous administration, for example, in each intravenous administration, an infusion administration time of the pharmaceutical composition is 30 min to 120 min, such as 60 min to 12 0 min or 60±15 min.

In some embodiments, the pharmaceutical composition is administered is once every four weeks or three weeks, such as once every three weeks.

In some embodiments, the therapeutically effective amount is 8 to 30 $mg/m^2$, such as 12 to 20 $mg/m^2$ or 20 $mg/m^2$, on the basis of mitoxantrone.

In a third aspect, the present application provides a pharmaceutical composition comprising mitoxantrone hydrochloride liposome for use in the treatment of ovarian cancer, gastric cancer, or head and neck squamous carcinoma.

In some embodiments, mitoxantrone hydrochloride liposome is the only active ingredient in the pharmaceutical composition.

In some embodiments, the pharmaceutical composition or the mitoxantrone hydrochloride liposome has one or more of the following properties:

(i) the mitoxantrone hydrochloride liposome having a particle size of about 30 to 80 nm, such as about 35 to 75 nm, about 40 to 70 nm, about 40 to 60 nm, or about 60 nm;

(ii) the mitoxantrone hydrochloride interacting with a multivalent counter ion (e.g., sulfate, citrate or phosphate) in the liposome to form a poorly soluble precipitate;

(iii) a phospholipid bilayer in the mitoxantrone hydrochloride liposome containing a phospholipid having a phase transition temperature (Tm) higher than body temperature, such that the liposome has a phase transition temperature higher than body temperature, for example, the phospholipid being selected from the group consisting of hydrogenated soy phosphatidylcholine, phosphatidylcholine, hydrogenated egg yolk lecithin, dipalmitate lecithin, distearate lecithin, or any combination thereof, (iv) a phospholipid bilayer in mitoxantrone hydrochloride liposome containing hydrogenated soy phosphatidylcholine, cholesterol and PEG2000 modified distearoylphosphatidylethanolamine (DSPE-PEG2000).

In some embodiments, a phospholipid bilayer in the mitoxantrone hydrochloride liposome contains hydrogenated soy phosphatidylcholine, cholesterol and PEG2000 modified distearoylphosphatidylethanolamine in a mass ratio of about 3:1:1, the mitoxantrone hydrochloride interacts with a multivalent acid ion in the liposome to form a poorly soluble precipitate, and the mitoxantrone hydrochloride liposome has a particle size of about 60 nm in the medicament.

In some embodiments, the ovarian cancer is platinum-refractory or platinum-resistant recurrent ovarian cancer.

In some embodiments, the gastric cancer is advanced gastric cancer.

In some embodiments, the head and neck squamous cell carcinoma is a squamous cell carcinoma occurring in a nasal cavity, sinus, nasopharynx, oropharynx, laryngopharynx, cervical esophagus, thyroid, salivary gland, oral cavity, larynx and/or ear.

In some embodiments, the head and neck squamous cell carcinoma is recurrent or metastatic head and neck squamous cell carcinoma that has undergone a first line therapy failure, for example, the first line therapy is a combination therapy of cisplatin or carboplatin and 5-FU or paclitaxel, optionally further in combination with cetuximab.

In some embodiments, the pharmaceutical composition is in the form of an injection, such as a liquid injection, a powder for injection, or a tablet for injection.

In some embodiments, the pharmaceutical composition is a liquid injection.

In some embodiments, the active ingredient content of the pharmaceutical composition is 0.5 to 5 mg/ml, such as 1 to 2 mg/ml or 1 mg/ml, on the basis of mitoxantrone.

DETAILED DESCRIPTION OF THE INVENTION

Mitoxantrone hydrochloride is an anthraquinone antitumor drug. The indications approved by the FDA are multiple sclerosis, prostate cancer, and acute myeloid leukemia. Clinical studies have shown some efficacy against malignant lymphoma, breast cancer, acute myeloid leukemia, lung cancer, melanoma, soft tissue sarcoma, multiple myeloma, liver cancer, colorectal cancer, renal cancer, prostate cancer, endometrial cancer, testicular tumors, ovarian cancer, and head and neck cancer. The clinical administration dose of mitoxantrone hydrochloride is limited due to relatively serious side effects such as bone marrow suppression, leukopenia and thrombocytopenia (dose-limiting toxicity), palpitations, premature beats, or abnormal electrocardiograms Usually, mitoxantrone hydrochloride needs to be used in combination with other drugs. However, previous studies shown that the efficacy of these combination regimens was not ideal. How to further improve the anti-tumor efficacy without causing serious toxic and side effects is a challenge in the clinical application of mitoxantrone hydrochloride.

Liposome is a novel form of drug carriers. In pharmaceutical definitions, liposomal drugs generally refer to microvesicles formed by encapsulating a drug within a lipid bilayer. Studies have shown that liposomal drugs can alter the in vivo distribution of an encapsulated drug, allowing the drug to accumulate primarily in tissues and organs such as liver, spleen, lung, and bone marrow, thereby increasing the therapeutic index, reducing the therapeutic dose, and reducing the toxicity. These characteristics make the application of liposome-loaded medicine more and more important in the research of antitumor drugs. The researchers of the applicant of the present application conducted studies on mitoxantrone liposomal formulations. For example, Chinese Patent Application No. 200610102339.8 filed on Dec. 29, 2006 and PCT Publication No. WO 2008/080367A1 filed on Dec. 29, 2007 disclose a mitoxantrone liposome. The disclosures of the above two references are incorporated herein in their entireties for all purposes.

A mitoxantrone liposomal preparation is a special preparation and is different from ordinary mitoxantrone injections. Its absorption, distribution and metabolism behaviors after entering the body are substantially different. Therefore, it is difficult to derive an appropriate treatment regimen according to the indication for the compound among different indications or among different tumor types. Thus, efficacy and indications for mitoxantrone liposomal formulations should be studied independently. For this purpose, the present inventors had thoroughly studied the efficacy of mitoxantrone liposome formulations in refractory ovarian cancer, gastric cancer or head and neck squamous carcinoma, and established the various inventions in the present application.

In the following detailed description, unless defined otherwise, all scientific and technical terms used herein have the same meaning as understood by one of ordinary skill in the art.

Although the numerical ranges and parameter approximations are shown in their broad ranges in the present application, the numerical values shown in the particular embodiments are described as accurately as possible. However, any numerical values inherently contain certain errors due to the standard deviation present in their respective measurements. Additionally, all ranges disclosed herein are to be understood as encompassing any and all subranges contained therein. For example, a described range of "1 to 10" should be considered to encompass any and all subranges between the minimum value of 1 and the maximum value of 10, inclusive, i.e., all subranges starting with the minimum value of 1 or a greater value, such as 1 to 6.1, and subranges ending with the maximum value of 10 or a less value, such as 5.5 to 10. When "about" is used herein for a numerical value or a range of numerical values, it represents the degree of floating of the numerical value acceptable in the art, and generally means±10% based on the numerical value or range of numerical values, such as ±9%, or ±8%, or ±7%, or ±6%, or ±5%, or ±4%, or ±3%, or ±2%, or ±1%.

As used herein, the term "pharmaceutical composition" means a combination of at least one drug, and optionally a pharmaceutically acceptable carrier or adjuvant, for working together to achieve a certain pharmaceutical purpose. In the technical context of liposomal formulations of the present application, pharmaceutically acceptable carriers are generally aqueous carriers, for example, water, aqueous buffers, isotonic saline solutions (e.g., physiological saline or phosphate buffered saline (PBS)), or sugar solutions. While, in the context of the present application, an injection is a suitable formulation form (and thus there are corresponding types of pharmaceutically acceptable carriers), it will be appreciated by those skilled in the art that other types of pharmaceutically acceptable carriers may be selected where other formulation forms are possible (e.g., oral formulations).

As used herein, a "therapeutically effective amount" or "effective amount" refers to a dose sufficient to show benefit to the subject being treated. The actual amount to be administered, as well as the rate and duration of administration, will depend on the condition and disease severity of the subject to be treated. The prescription of treatment (e.g., decision on dosage) is ultimately determined by physicians, who generally take into account the disease being treated, the condition of the individual patient, the site of delivery, the method of administration, and other factors known to the physician.

"Individuals", "subjects", or "patients" described herein include all members of the animal community, including, but not limited to, mammals (e.g., mice, rats, cats, monkeys, dogs, horses, or pigs.) and humans. Preferably, a subject is a human subject. The terms "individuals", "subjects", and "patients" may be used interchangeably unless indicated.

1. Mitoxantrone Hydrochloride Liposome and Formulations

Mitoxantrone hydrochloride (Mitoxantrone HCl) is an anthraquinone antitumor drug having the following structure:

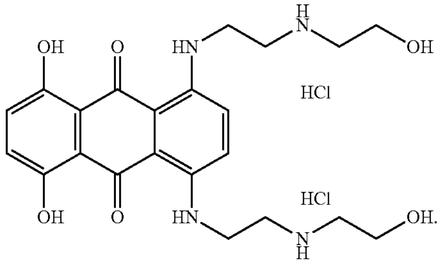 [SMILES: O=C1c2c(O)ccc(O)c2C(=O)c2c(NCCNCCO)ccc(NCCNCCO)c21 ; Cl ; Cl]

Broadly, liposome is an artificial membrane. In water, the hydrophilic head of a phospholipid molecule is inserted into the water, the hydrophobic tail of the liposome extends to the air, and a spherical liposome of the bilayer lipid molecules is formed after agitation. In the field of biomedicine, liposome is commonly used in transgenic techniques or in the preparation of drugs. Liposome can be fused to cell membranes to deliver drugs inside cells. In pharmaceutical definitions, liposomal drugs generally refer to microvesicles formed by encapsulating a drug within a lipid bilayer. The chemical composition of liposome generally includes phospholipids (including natural and synthetic phospholipids) and cholesterol.

Preparation techniques for liposomal pharmaceutical formulations have been reported in the art. Those skilled in the art can find technical guidance for the preparation of mitoxantrone hydrochloride liposomal formulations.

In some embodiments, mitoxantrone hydrochloride liposome is the only active ingredient in a drug.

In the technical background of the present application, the present inventors had found that the mitoxantrone hydrochloride liposome formulations prepared by the method disclosed in Chinese Patent Application No. 200610102339.8 or PCT Publication No. WO 2008/080367A1 had good efficacy.

Without being bound by any particular theory, the present inventors of the present application had found that one or more or all of the following properties are advantageous for a mitoxantrone hydrochloride liposome formulation Firstly, in liposomal formulations/drugs, the particle size of mitoxantrone hydrochloride liposome is about 30 to 80 nm, for example about 30, 25, 40, 45, 50, 55, 60, 65, 70, 75 or 80 nm. More suitable ranges include about 35 to 75 nm, about 40 to 70 nm, and about 40 to 60 nm. In one example (see Examples hereinafter), the particle size of mitoxantrone hydrochloride liposome is about 60 nm. The particle size can be measured in a variety of ways, including but not limited to NanoZS.

Secondly, mitoxantrone hydrochloride interacts with multivalent counterions (e.g., sulfate, citrate, or phosphate) within the liposome to form a poorly soluble precipitate.

Thirdly, the phospholipid bilayer in mitoxantrone hydrochloride liposome contains phospholipids having a phase transition temperature (Tm) higher than the body temperature (e.g., 36 to 38° C.), so that the phase transition temperature of the liposome is higher than the body temperature. Phospholipid molecules are essential components of liposome, liposome formed from different kinds of phospholipid molecules has solid-gel-liquid phase transition properties at different temperatures, and the composition of the phospholipids largely determines the phase transition temperature of the liposome. Phospholipid species suitable for achieving the desired phase transition temperatures herein include, but are not limited to, hydrogenated soy phosphatidylcholine, phosphatidylcholine, hydrogenated egg yolk lecithin, bispalmitate lecithin, bisstearate lecithin, or any combination thereof. In addition, one skilled in the art can select other suitable phospholipid species and combination proportions based on phase transition temperature tests. In some embodiments, in addition to cholesterol, the phospholipid bilayer of mitoxantrone hydrochloride liposome of the present application contains phospholipid molecules including hydrogenated soybean lecithin and PEG2000 modified distearoylphosphatidylethanolamine (DSPE-PEG2000).

In some embodiments, the phospholipid bilayer in the mitoxantrone hydrochloride liposome contains hydrogenated soy phosphatidylcholine, cholesterol and PEG2000 modified distearoylphosphatidylethanolamine in a mass ratio of about 3:1:1, the mitoxantrone hydrochloride interacts with a multivalent acid ion within the liposome to form a poorly soluble precipitate, and the particle size of the mitoxantrone hydrochloride liposome in a drug is about 60 nm.

In liposomal pharmaceutical formulations, "lipid-to-drug ratio" refers to the mass ratio of the components (including phospholipids and cholesterol) of the phospholipid bilayer in the liposome to the drug (mitoxantrone in the present application). For example, in an exemplary formula of a liposomal pharmaceutical formulation of the present application, the lipid-to-drug ratio refers to the mass ratio of the components of the phospholipid bilayer (including HSPC, DSPE-PEG2000, and Chol) in the liposome to the mitoxantrone.

By way of non-limiting example, the mitoxantrone hydrochloride liposomal formulations of the present application can be prepared according to the following protocols.

Hydrogenated soy phosphatidylcholine (HSPC), cholesterol (Chol) and PEG2000 modified distearoylphosphatidylethanolamine (DSPE-PEG2000) are weighed at a mass ratio of 3:1:1 and dissolved in 95% ethanol to yield a clear solution (i.e., an ethanol solution of phospholipids). The ethanol solution of phospholipids is mixed with a 300 mM ammonium sulfate solution. After shaking for 1 h at 60 to 65° C. for hydration, heterogeneous multi-compartment liposome is obtained. The particle size of the liposome is then reduced using a microfluidic device. The obtained sample is diluted 200 times with a 0.9% NaCl solution, and detected with NanoZS. The average particle size of the particles is about 60 nm. The main peak is concentrated between 40 to 60 nm. The ammonium sulfate of the outer phase of the blank liposome is then removed using an ultrafiltration device and the outer phase is replaced with 290 mM sucrose and 10 mM glycine to form a transmembrane ammonium sulfate gradient. A solution of mitoxantrone hydrochloride (10 mg/mL on the basis of mitoxantrone) is added to the blank liposome in a lipid-to-drug ratio of 16:1 at drug loading temperature of 60 to 65° C. After incubation for about 1 h, the encapsulation efficiency can be demonstrated to be about 100% using gel exclusion chromatography. The product thus obtained is named PLM60 and used in the Examples described hereinafter. The weight ratio of HSPC:Chol:DSPE-PEG2000:mitoxantrone in PLM60 is 9.58:3.19:3.19:1. The osmolality of the sucrose glycine solution is close to the physiological value.

It will be appreciated that the various technical details and parameters in the above exemplary preparation methods may be adjusted and determined by those skilled in the art within reasonable extents. For example, amino acids, which can be used to replace glycine in the outer phase used to form a transmembrane ammonium sulfate gradient include, but are not limited to, histidine, asparagine, glutamic acid, leucine, proline, and alanine. For another example, the mass ratios of HSPC, Chol, and DSPE-PEG2000 may be adjusted appropriately. For a further example, for lipid-to-drug ratios in the preparation of specific liposomal pharmaceutical formulations, one skilled in the art can design, test, and ultimately determine suitable lipid-to-drug ratios to maximize drug loading while reducing drug leakage. For the mitoxantrone hydrochloride liposomal formulations of the present application, lipid-to-drug ratios that can be used are in wide ranges, e.g., as low as 2:1 or as high as 30:1, 40:1, or 50:1, and more suitable lipid-to-drug ratios can be about (15 to 20): 1, e.g., about 15:1, 16:1, 17:1, 18:1, 19:1, or 20:1. Thus, the several advantageous properties of the mitoxantrone hydrochloride liposomal formulations described above are more important, while there are various methodologies for achieving these properties.

2. Indications

In the present application, the indications of mitoxantrone hydrochloride liposomal formulations include ovarian cancer, gastric cancer, and head and neck squamous cell carcinoma. The first-line, second-line, or second or upper-line drugs for the treatment of ovarian cancer, gastric cancer, and head and neck squamous cell carcinoma referred to in the present application refer to the first-line, second-line, or second or upper-line drugs for the treatment of ovarian cancer, gastric cancer, or head and neck squamous cell carcinoma approved by the drug management department in China and other jurisdictions (such as the United States, the European Union, Japan, or Korea), including, but not limited to, FDA-approved bevacizumab, PD-1 inhibitors, trastuzumab, and apatinib.

2.1 Ovarian Cancer

In some embodiments, the indication of the mitoxantrone hydrochloride liposomal formulation is ovarian cancer. In some embodiments, the mitoxantrone hydrochloride liposome serves as the only active ingredient in the medicaments/pharmaceutical compositions of the present application for the treatment of ovarian cancer.

In some embodiments, the ovarian cancer is platinum-refractory or platinum-resistant recurrent ovarian cancer. Platinum-refractory or platinum-resistant recurrent ovarian cancer refers to a platinum-refractory or platinum-resistant recurrent ovarian cancer that at least has failed a standard platinum-based regimen.

Suitable pharmaceutical dosage forms are injectable dosage forms, including liquid injections, powders for injection and tablets for injection. If the drug is a liquid injection, the active ingredient content of the drug is 0.5 to 5 mg/ml on the basis of mitoxantrone, and more suitable ranges include 1 to 2 mg/ml or 1 mg/ml.

During treatment, on the basis of mitoxantrone, a therapeutically effective amount is generally 8 to 30 $mg/m^2$ calculated based on the surface area of a subject, and more suitable ranges include 12 to 20 $mg/m^2$, e.g., 12 $mg/m^2$, 14 $mg/m^2$, 16 $mg/m^2$, 18 $mg/m^2$, or 20 $mg/m^2$.

A suitable administration mode for the mitoxantrone hydrochloride liposomal formulations of the present application is intravenous administration. In some embodiments, the administration frequency is once every four weeks or three weeks. In some embodiments, for each time of intravenous administration, the liposomal pharmaceutical formulation is administered during 30 min to 120 min, and more suitable ranges include 60 min to 120 min and 90±15 min.

2.2 Gastric Cancer

In some embodiments, the indication of the mitoxantrone hydrochloride liposomal formulation is gastric cancer. In some embodiments, mitoxantrone hydrochloride liposome serves as the only active ingredient in the medicaments/pharmaceutical compositions of the present application for the treatment of gastric cancer.

In some embodiments, the gastric cancer is advanced gastric cancer. Advanced gastric cancer refers to advanced gastric cancer which has been diagnosed histopathologically and has a metastasis, including carcinoma at the gastroesophageal junction.

Suitable pharmaceutical dosage forms are injectable dosage forms, including liquid injections, powders for injection and tablets for injection. If the drug is a liquid injection, the active ingredient content of the drug is 0.5 to 5 mg/ml on the basis of mitoxantrone, and more suitable ranges include 1 to 2 mg/ml or 1 mg/ml.

During treatment, on the basis of mitoxantrone, a therapeutically effective amount is generally 8 to 30 $mg/m^2$ calculated based on the surface area of a subject, and more suitable ranges include 12 to 20 $mg/m^2$, e.g., 12 $mg/m^2$, 14 $mg/m^2$, 16 $mg/m^2$, 18 $mg/m^2$, or 20 $mg/m^2$.

A suitable administration mode for the mitoxantrone hydrochloride liposomal formulations of the present application is intravenous administration. In some embodiments, the administration frequency is once every four weeks or three weeks. In some embodiments, for each time of intravenous administration, the liposomal pharmaceutical formulation is administered during 30 min to 120 min, and more suitable ranges include 60 min to 120 min and 90±15 min.

2.3. Head and Neck Squamous Cell Carcinoma

In some embodiments, the indication of the mitoxantrone hydrochloride liposomal formulation is head and neck squamous cell carcinoma. In some embodiments, mitoxantrone hydrochloride liposome serves as the only active ingredient in the medicaments/pharmaceutical compositions of the present application for the treatment of head and neck squamous cell carcinoma.

Head and neck squamous cell carcinoma includes squamous cell carcinoma occurring in a nasal cavity, sinus, nasopharynx, oropharynx, laryngopharynx, cervical esophagus, thyroid, salivary gland, oral cavity, larynx and/or ear, among which nasopharyngeal carcinoma is the type of cancer of particular interest in the present application.

In some embodiments, the head and neck squamous cell carcinoma is recurrent/metastatic head and neck squamous cell carcinoma. In some embodiments, the head and neck squamous cell carcinoma is recurrent/metastatic head and neck squamous cell carcinoma that has undergone a first-line therapy failure. In some embodiments, the combination of cisplatin with 5-fluorouracil (5-FU) (the PF regimen) or the combination of cisplatin with paclitaxel is a common option for first-line chemotherapy regimens. If the patient is not suitable for cisplatin treatment, carboplatin may be used instead. The above-mentioned first-line treatment regimens can be combined with cetuximab.

Suitable pharmaceutical dosage forms are injectable dosage forms, including liquid injections, powders for injection and tablets for injection. If the drug is a liquid injection, the active ingredient content of the drug is 0.5 to 5 mg/ml on the basis of mitoxantrone, and more suitable ranges include 1 to 2 mg/ml or 1 mg/ml.

During treatment, on the basis of mitoxantrone, a therapeutically effective amount is generally 8 to 30 $mg/m^2$ calculated based on the surface area of a subject, and more suitable ranges include 12 to 20 $mg/m^2$, e.g., 12 $mg/m^2$, 14 $mg/m^2$, 16 $mg/m^2$, 18 $mg/m^2$, or 20 $mg/m^2$.

A suitable administration mode for the mitoxantrone hydrochloride liposomal formulations of the present application is intravenous administration. In some embodiments, the administration frequency is once every four weeks or three weeks. In some embodiments, for each time of intravenous administration, the liposomal pharmaceutical formulation is administered during 30 min to 120 min, and more suitable ranges include 60 min to 120 min and 90±15 min.

3. Dosing Regimens

As described above, liposomal drug formulations belong to a particular drug type. The absorption, distribution, and metabolism of a liposomal drug after it enters the body may be different as compared to a free drug. Thus, dosing regimens based on design and testing for a free drug are not necessarily suitable for liposomal formulations containing the same drug. Similarly, the dosage regimen determined for a liposomal pharmaceutical formulation in the design and testing for a particular cancer is not necessarily applicable to the administration of the liposomal pharmaceutical formulation in other types of cancer.

Previous studies have shown that the safe and effective dose of a single drug may vary considerably in the treatment of different indications, as exemplified below.

Doxil (a doxorubicin hydrochloride liposomal formulation) has three indications approved by FDA, i.e., (1) ovarian cancer with a recommended dose of 50 $mg/m^2$ by intravenous administration every four weeks; (2) Kaposi's sarcoma with a recommended dose of 20 $mg/m^2$ by intravenous administration every three weeks; and (3) multiple myeloma with a recommended dose of 30 $mg/m^2$ by intravenous administration on the fourth day after administration of bortezomib.

Abraxane (a paclitaxel for injection [Albumin-Binding]) has three indications approved by FDA with different dosing regimens, i.e., (1) metastatic breast cancer with a recommended dose of 260 $mg/m^2$ by intravenous drip for 30 minutes, once every three weeks; (2) non-small cell lung cancer with a recommended dose of 100 $mg/m^2$ by intravenous drip for 30 minutes and a therapeutic course of 21 days with administration on Days 1, 8 and 15, respectively (on Day 1, immediately after administration of the paclitaxel for injection (albumin-binding), carboplatin is administered and then administered once every 21 days); and (3) pancreatic cancer with a recommended dose of 125 $mg/m^2$ by intravenous drip for 30-40 minutes and a therapeutic course of 28 days with administration on Days 1, 8 and 15, respectively (for each time of therapy, immediately after administration of the paclitaxel for injection (albumin-binding), gemcitabine is administered).

AmBisome (an amphotericin B liposomal formulation for injection) has different indications with different starting doses. For empirical treatment, the recommended dose is 3 mg/kg/day. For the treatment of systemic fungal infection (*Aspergillus, Candida*, or *Cryptococcus*), the recommended dose is 3 to 5 mg/kg/day. For treating cryptococcal meningitis in HIV-infected patients, the recommended doses are 6 mg/kg/day (Days 1 to 5), and 3 mg/kg/day (Days 4 and 21). For treating immunocompromised visceral leishmaniasis patients, the recommended doses are 4 mg/kg/day (Days 1 to 5), and 4 mg/kg/day (Days 10, 17, 24, 31, and 38). It can be seen that there are differences in the safe and effective doses of a single drug for different indications. The doses and administration regimens are personalized according to the particular disease species and the actual condition of the patient, in order to achieve maximum efficacy and minimal toxic or adverse effects, and finally to achieve safe and effective treatment of the disease.

Thus, for the mitoxantrone hydrochloride liposomal formulations of the present application, there may also be different optimal administration regimens for different types of cancer.

EXAMPLES

The present application is further illustrated in reference to below Examples. It is to be understood that these Examples are merely illustrative of the present application and are not intended to limit the scope of the present application. Experimental methods not specified in details in the following Examples are generally according to conventional conditions, or according to protocols suggested by manufacturers.

Example 1

The inventors of the present application tested the efficacy of the mitoxantrone hydrochloride liposomal fomulation PLM60 in animal model-based experiments of ovarian cancer, gastric cancer, and head and neck squamous cell carcinoma. The results showed that (not shown in the present application) PLM60 was effective in treating ovarian cancer, gastric cancer, and head and neck squamous cell carcinoma. The compound represented by Formula 1 was prepared as a light brown solid with reference to the method described in Example 22 in patent reference WO2016023330A1.

Example 2

Clinical Study of Mitoxantrone Hydrochloride Liposome Injection in Treatment of Platinum-Refractory or Platinum-Resistant Recurrent Ovarian Cancer The study in this Example is a single-arm, open-label, multicenter phase I b study in which subjects recruited were treated with the mitoxantrone hydrochloride liposome injection (PLM60) to evaluate the safety and efficacy of the mitoxantrone hydrochloride liposome injection in subjects with platinum-refractory or platinum-resistant recurrent ovarian cancer.

Abbreviations are used in this and subsequent Examples, which are complete response (CR), partial response (PR), stable disease (SD), objective response rate (ORR), and disease control rate (DCR).

I. Trial Design

1. Trial Protocols

All recruited subjects were treated with mitoxantrone hydrochloride liposome injections alone at a dose of 20 $mg/m^2$ once every three weeks (q3w). The study plan included recruiting not less than 30 subjects. 28 days prior to administration, screening tests were completed and baseline assessments were performed. After determining inclusion/exclusion criteria, the recruited subjects received therapies. All recruited subjects received 8 treatment courses. The treatment could be discontinued when disease progression (PD), intolerable toxicity, or death was observed, or continued benefit could not be obtained as judged by the researchers. For subjects who had undergone 8 treatment courses, if they could still obtain therapeutic benefits and the therapy was tolerable to them, the researchers might consult with the trial organizer to determine whether treatment could be continued, in order to observe and evaluate preliminary efficacy and safety.

Each subject's trial includes a screening period, a treatment period and a follow-up period.

After the subjects signed the informed consent form and completed all baseline tests during the screening period, subjects qualified for recruitment were treated with mitoxantrone hydrochloride injections in the order of recruitment. According to the protocols, all subjects received tests specified in the protocols throughout the trial treatment period to assess safety.

2. Study Duration

The study included a screening period of four weeks (28 days), and a treatment period of 8 courses (24 weeks). A follow-up for safety was done four weeks (28 days) after the final dose. Then, PFS follow-ups were done every six weeks, and survival follow-ups were done every six weeks after disease progression. The study duration for each patient was expected to approximately 12 months.

The study plan included recruiting not less than 30 subjects, and the entire duration of the study is expected to be 24 to 36 months.

II. Trial Cohort:

Subjects who met all of the following inclusion criteria and none of the exclusion criteria were recruited in this clinical study.

(1) Inclusion Criteria

Subjects must meet all of the following criteria.

1) voluntarily participating in the study and signing an informed consent form;

2) being female subjects aged 18 years;

3) histopathologically diagnosed for epithelial ovarian cancer, fallopian tube cancer, or primary peritoneal cancer (except for low-grade serous and mucinous cancer);

4) being a platinum-refractory or platinum-resistant relapse subject who at least had failed treatment with a standard platinum-based regimen;

5) bearing at least one measurable lesion that met the definition of RECIST 1.1 at the baseline;

6) having a ECOG score of 0-2;

7) having expected survival time≥three months;

8) Recovering to grade≤1 (except for alopecia, pigmentation, or other toxicity considered not to be a safety risk for the subject in the study) from toxicity due to previous anti-tumor treatments;

9) having the following measurements in the laboratory tests:

absolute neutrophil count (ANC) $1.5\times10^9$/L (no G-CSF boosting therapy within one week prior to the laboratory tests);

hemoglobin (Hb)≥9.0 g/dL (no erythrocyte transfusion therapy within one week prior to the laboratory tests);

platelets≥$75\times10^9$/L (no transfusion of platelets, thrombopoietin, interleukin-11, or other drugs that elevated platelet level within one week prior to the laboratory tests);

creatinine≤1.5×ULN;

total bilirubin≤1.5×ULN (≤3×ULN for patients with liver metastasis);

alanine aminotransferase (ALT)/aspartate aminotransferase (AST) 2.5×ULN (≤5×ULN for patients with liver metastasis);

albumin≥3.0 g/dL;

coagulation with prothrombin time (PT) and international normalized ratio (INR)≤1.5×ULN;

10) being urine or blood HCG negative (except for ones who were at menopause or received hysterectomy) for female subjects, and for those at childbearing age, being able to adopt effective contraception measures (e.g., hormone combination (including estrogen and progestin) in combination with inhibition of ovulation, progestin contraception in combination with inhibition of ovulation, intrauterine device, intrauterine hormone release system, bilateral tubal ligation, vasectomy, or avoidance of sexual behaviour) with their spouses during the trial and within six months after the final dose; and 11) being able to communicate well with the researchers and to understand and voluntarily comply with the requirements of the study.

(II) Exclusion Criteria:

Subjects meeting any one of the following criteria were excluded from this trial.

1) having severe allergy to mitoxantrone or liposome;

2) having brain or meningeal metastasis;

3) having clinically symptomatic pericardial effusion;

4) having received allogeneic organ transplantation or allogeneic bone marrow transplantation;

5) having active hepatitis B (HbsAg or HBcAb positive and HBV DNA≥2000 IU/mL), or active hepatitis C (HCV antibody positive and HCV RNA level above the lower limit detectable by the research center), or being HIV antibody positive;

6) having active bacterial infection, fungal infection, viral infection or interstitial pneumonia requiring systemic treatment within one week prior to the first dose;

7) having received any antitumor treatment within four weeks prior to the first dose;

8) having received treatment with a drug in another clinical study within four weeks prior to the first dose;

9) having received major surgery within three months prior to the first dose (surgical grade of 3-4, except for intravenous port implantation), or having plans to receive major surgery during the study;

10) having thrombotic or embolic events such as cerebrovascular accidents (including transient ischemic attacks), or pulmonary embolism in the last six months;

11) having other active malignant tumors in the last three years, except for cured local treatable cancer such as basal or squamous cell skin cancer, superficial bladder cancer, or in situ prostate, cervix or breast cancer;

12) having cardiac dysfunction characterized by:
   long QTc syndrome or QTc interval>480 ms;
   complete left bundle branch block, or degree II or III atrioventricular block;
   severe and uncontrolled arrhythmias requiring medical treatment;
   NYHA≥grade 3;
   cardiac ejection fraction below 50% or below the lower limit detectable by the research center;
   CTCAE>2 cardiac valvular disease;
   uncontrolled hypertension (defined as systolic blood pressure>150 mmHg or diastolic blood pressure>90 mmHg in multiple measurements with drug management); or
   myocardial infarction, unstable angina, a history of severe pericardial disease, electrocardiographic evidence of acute ischemic or active conduction system abnormalities occurred within six months prior to screening.
13) having received treatment with doxorubicin or other anthracyclines with cumulative doxorubicin doses in excess of 350 $mg/m^2$ (equivalent dose calculation for anthracyclines: 1 mg doxorubicin=2 mg epirubicin=2 mg daunorubicin=0.5 mg nordoxorubicin=0.45 mg mitoxantrone);
14) being pregnant or lactating;
15) having any serious and/or uncontrollable disease that, in the judgment of the researchers, may affect the patient's participation in the study (including, but not limited to, uncontrolled diabetes, kidney disease requiring dialysis, severe liver diseases, life-threatening auto-immune system diseases and hemorrhagic diseases, drug abuse, and nervous system diseases); and
16) having other factors unfit to participate in the study as judged by the researchers.

(III) Withdrawal/Termination Criteria

Subjects who experienced any of the following events during the study course were discontinued from treatment with the test drug.

1) The subject experienced intolerable toxicity and the researchers believed that the risk in continuing the treatment with study drug outweighs the benefit.
2) Disease progression was observed by imaging assessment.
3) Clinically assessed disease progression was observed, major protocol violation incurred, or the subject had poor compliance, which, in the judgment of the researchers, would not lead to benefit from continued therapy with the test drug.
4) The subject got pregnancy.
5) The subject was dead.
6) The subject meet any of the withdrawal criteria.

All subjects who withdrew from the treatment would still be followed up according to the study protocols, with the exception that subject death is the cause for discontinued treatment, or a subject met any of the following criteria for withdrawal from the study.

Subjects had the right to withdraw from the study at any time for any reason. Subjects would withdraw from the study if any of the following events occurs.

1) The subject is lost from follow-up.
2) The subject withdrew consent or the subject or his/her family member requested the subject to withdraw from the trial.
3) The study terminated.
4) Other III. Study Results Subjects were evaluated for efficacy according to RECIST 1.1 criteria, and were evaluated for all adverse events according to CTCAE 5.0 criteria.

The inventors of the present application tested mitoxantrone liposome. The drug, after entering a human body by intravenous infusion, had the effects of slow release, targeted action, attenuation, and enhanced efficacy. The administered dose was higher than that of a common injection. As a single-agent treatment, administration of mitoxantrone liposome could improve the efficacy and reduce the occurrence rate of adverse effects.

A total of 47 subjects were recruited as of Oct. 31, 2021 (the study continued up to now), including 13 platinum-refractory cases and 34 platinum-resistant cases. 39 subjects received at least one efficacy evaluation with the overall ORR being 17.9% (7/39) and the DCR being 59.0% (23/39). Among patients who were platinum-resistant and had received third or above-line treatment, a total of 24 subjects received at least one efficacy evaluation with the ORR being 29.2% (7/24) and the DCR being 62.5% (15/24). No intolerable adverse effects were observed in all subjects.

According to the experimental results up to now, the mitoxantrone hydrochloride liposomal formulation of the present application could improve the treatment regimen of ovarian cancer, and lay a foundation for the subsequent combination therapy to beat the first-line and second-line treatment.

Example 3

Clinical Study of Mitoxantrone Hydrochloride Liposome Injection in the Treatment of Advanced Gastric Cancer The study in this Example is a single-arm, open-label, multicenter phase I b study in which subjects recruited were treated with the mitoxantrone hydrochloride liposome injection (PLM60) to evaluate the safety and efficacy of the mitoxantrone hydrochloride liposome injection in subjects with advanced gastric cancer.

I. Trial Design

1. Trial Protocols

All recruited subjects were treated with mitoxantrone hydrochloride liposome injections alone at a dose of 20 $mg/m^2$ once every three weeks (q3w). The study plan included recruiting 30 to 60 subjects (male or female) with advanced gastric cancer. 28 days prior to administration, screening tests were completed and baseline assessments were performed. After determining inclusion/exclusion criteria, the recruited subjects received therapies. All recruited subjects received maximal 8 treatment courses. The treatment could be discontinued when disease progression (PD), intolerable toxicity, or death was observed, or continued benefit could not be obtained as judged by the researchers. Administration might be delayed after the second course, but the delay should not exceed three weeks. A dose adjustment could be done after the second course to a minimum dose of 12 $mg/m^2$. Safety evaluation and efficacy evaluation were performed after administration according to the protocols. Follow-ups were performed 28 days after the final dose. Subjects who early withdrew from the trial should be followed up, wherever possible, after the final dose. After the final dose, the follow-up period started. Tumor assessments were continued every six weeks for subjects withdrew from the study for reasons except for observation of radiographically assessed disease progression or receipt of a new anti-tumor therapy, until disease progression was observed.

Survival follow-ups were performed every six weeks when the subject developed radiologically assessed disease progression or started to receive a new antitumor therapy.

Each subject's trial includes a screening period, a treatment period and a follow-up period.

After the subjects signed the informed consent form and completed all baseline tests during the screening period, subjects qualified for recruitment were treated with mitoxantrone hydrochloride injections in the order of recruitment. According to the protocols, all subjects received tests specified in the protocols throughout the trial treatment period to assess safety.

2. Study Duration

The study included a screening period of four weeks (28 days), and a treatment period of maximal 8 courses (24 weeks). A follow-up for safety was done four weeks (28 days) after the final dose. Then, PFS follow-ups were done every six weeks, and survival follow-ups were done every six weeks after disease progression. The study duration for each patient was expected to approximately 12 months.

The study plan included recruiting 30 to 60 subjects, and the entire duration of the study is expected to be 24 to 36 months.

II. Trial Cohort:

Subjects who met all of the following inclusion criteria and none of the exclusion criteria were recruited in this clinical study.

(1) Inclusion Criteria

Subjects must meet all of the following criteria.

1) voluntarily participating in the study and signing an informed consent form;
2) aged≥18 years for both male and female;
3) histopathologically diagnosed for metastatic advanced gastric cancer (including cancer incurring at the gastroesophageal junction);
4) being assessed by researchers as subjects suitable for treatment with mitoxantrone hydrochloride liposome injection;
5) bearing at least one measurable lesion that met the definition of RECIST 1.1 at the baseline;
6) having a ECOG score of 0-2;
7) having expected survival time≥three months;
8) Recovering to grade≤1 (except for alopecia, pigmentation, or other toxicity considered not to be a safety risk for the subject in the study) from toxicity due to previous anti-tumor treatment;
9) having the following measurements in the laboratory tests:
   - absolute neutrophil count (ANC)≥$1.5\times10^9$/L (no G-CSF boosting therapy within one week prior to the laboratory tests);
   - hemoglobin (Hb)≥9.0 g/dL (no erythrocyte transfusion therapy within one week prior to the laboratory tests, and no erythropoietin therapy within two weeks prior to the laboratory tests);
   - platelets≥$75\times10^9$/L (no transfusion of platelets within one week prior to the laboratory tests, and no treatment with thrombopoietin, interleukin-11, or other drugs that elevated platelet level within two weeks prior to the laboratory tests);
   - creatinine≤1.5×ULN;
   - total bilirubin≤1.5×ULN (≤3×ULN for patients with liver metastasis);
   - alanine aminotransferase (ALT)/aspartate aminotransferase (AST)≤2.5× ULN (≤5×ULN for patients with liver metastasis);
   - albumin 3.0 g/dL;
   - coagulation with prothrombin time (PT) and international normalized ratio (INR) 1.5×ULN;
10) being urine or blood HCG negative (except for ones who were at menopause or received hysterectomy) for female subjects, and for those at childbearing age, being able to adopt effective contraception measures (e.g., hormone combination (including estrogen and progestin) in combination with inhibition of ovulation, progestin contraception in combination with inhibition of ovulation, intrauterine device, intrauterine hormone release system, bilateral tubal ligation, vasectomy, or avoidance of sexual behaviour) during the trial and within six months after the final dose;
11) for male subjects, being able to adopt one of the contraception measures specified in item 10) with their spouses; and
12) being able to communicate well with the researchers and to understand and voluntarily comply with the requirements of the study.

(II) Exclusion Criteria:

Subjects meeting any one of the following criteria were excluded from this trial.

1) having severe allergy to mitoxantrone or liposome;
2) having brain or meningeal metastasis;
3) having gastric cancer which might be suitable for radical resection;
4) having significant clinical symptoms of pleural, pericardial, or peritoneal effusion (except for subject who were treated with drainage within 1 month prior to screening, had no significant clinical symptoms, and only had a small amount of effusion by imaging assessment);
5) Suffering from intestinal obstruction, having significant clinical symptoms and requiring intervention;
6) having gastrointestinal bleeding of CTCAE grade 3 to 4 within three months prior to the first dose;
7) having received allogeneic organ transplantation or allogeneic bone marrow transplantation;
8) having active hepatitis B (HbsAg or HBcAb positive and HBV DNA≥2000 IU/mL), or active hepatitis C (HCV antibody positive and HCV RNA level above the lower limit detectable by the research center), or being HIV antibody positive;
9) having active bacterial infection, fungal infection, viral infection or interstitial pneumonia requiring systemic treatment within one week prior to the first dose;
10) having received any antitumor treatment within four weeks prior to the first dose;
11) having received treatment with a drug in another clinical study within four weeks prior to the first dose;
12) having received major surgery within three months prior to the first dose (surgical grade of 3-4, except for intravenous port implantation), or having plans to receive major surgery during the study;
13) having thrombotic or embolic events such as cerebrovascular accidents (including transient ischemic attacks), or pulmonary embolism in the last six months;
14) having other active malignant tumors in the last three years, except for cured local treatable cancer such as basal or squamous cell skin cancer, superficial bladder cancer, or in situ prostate, cervix or breast cancer;
15) having cardiac dysfunction characterized by:
   - long QTc syndrome or QTc interval>480 ms;
   - complete left bundle branch block, or degree II or III atrioventricular block;
   - severe and uncontrolled arrhythmias requiring medical treatment;

NYHA≥grade 3;
cardiac ejection fraction below 50% or below the lower limit detectable by the research center;
CTCAE>2 cardiac valvular disease;
uncontrolled hypertension (defined as systolic blood pressure>150 mmHg or diastolic blood pressure>90 mmHg in multiple measurements with drug management); or
myocardial infarction, unstable angina, a history of severe pericardial disease, electrocardiographic evidence of acute ischemic or active conduction system abnormalities occurred within six months prior to screening.

16) having received treatment with doxorubicin or other anthracyclines with cumulative doxorubicin doses in excess of 350 mg/$m^2$ (equivalent dose calculation for anthracyclines: 1 mg doxorubicin=2 mg epirubicin=2 mg daunorubicin=0.5 mg nordoxorubicin=0.45 mg mitoxantrone);
17) being pregnant or lactating;
18) having any serious and/or uncontrollable disease that, in the judgment of the researchers, may affect the patient's participation in the study (including, but not limited to, uncontrolled diabetes, kidney disease requiring dialysis, severe liver diseases, life-threatening autoimmune system diseases and hemorrhagic diseases, drug abuse, and nervous system diseases); and
19) having other factors unfit to participate in the study as judged by the researchers.

(III) Withdrawal/Termination Criteria

Subjects who experienced any of the following events during the study course were discontinued from treatment with the test drug.

1) The subject experienced intolerable toxicity and the researchers believed that the risk in continuing the treatment with study drug outweighs the benefit.
2) Disease progression was observed by imaging assessment.
3) Clinically assessed disease progression was observed, major protocol violation incurred, or the subject had poor compliance, which, in the judgment of the researchers, would not lead to benefit from continued therapy with the test drug.
4) The subject got pregnancy.
5) The subject was dead.
6) The subject meet any of the withdrawal criteria.

All subjects who withdrew from the treatment would still be followed up according to the study protocols, with the exception that subject death is the cause for discontinued treatment, or a subject met any of the following criteria for withdrawal from the study.

Subjects had the right to withdraw from the study at any time for any reason. Subjects would withdraw from the study if any of the following events occurs.

1) The subject is lost from follow-up.
2) The subject withdrew consent or the subject or his/her family member requested the subject to withdraw from the trial.
3) The study terminated.
4) Other III. Study Results Subjects were evaluated for efficacy according to RECIST 1.1 criteria, and were evaluated for all adverse events according to CTCAE 5.0 criteria.

The inventors of the present application anticipated that mitoxantrone liposome, after entering a human body by intravenous infusion, had the effects of slow release, targeted action, attenuation, and enhanced efficacy. The administered dose was higher than that of a common injection. As a single-agent treatment, administration of mitoxantrone liposome could improve the efficacy and reduce the occurrence rate of adverse effects.

Example 4

Clinical Study of Mitoxantrone Hydrochloride Liposome Injection in the Treatment of Recurrent/Metastatic Head and Neck Squamous Cell Carcinoma The study in this Example is a single-arm, open-label, multicenter phase I b study in which subjects recruited were treated with the mitoxantrone hydrochloride liposome injection (PLM60) to evaluate the safety and efficacy of the mitoxantrone hydrochloride liposome injection in subjects with recurrent/metastatic head and neck squamous cell carcinoma.

I. Trial Design

1. Trial Protocols

All recruited subjects were treated with mitoxantrone hydrochloride liposome injections alone at a dose of 20 mg/$m^2$ once every three weeks (q3w). The study plan included recruiting not less than 30 subjects (male or female) with recurrent/metastatic head and neck squamous cell carcinoma. 28 days prior to administration, screening tests were completed and baseline assessments were performed. After determining inclusion/exclusion criteria, the recruited subjects received therapies. All recruited subjects received 8 treatment courses. The treatment could be discontinued when disease progression (PD), intolerable toxicity, or death was observed, or continued benefit could not be obtained as judged by the researchers. Administration might be delayed after the second course, but the delay should not exceed three weeks. A dose adjustment could be done after the second course to a minimum dose of 12 mg/$m^2$. Safety evaluation and efficacy evaluation were performed after administration according to the protocols. Follow-ups were performed 28 days after the final dose. Subjects who early withdrew from the trial should be followed up, wherever possible, after the final dose.

After the final dose, the follow-up period started. Tumor assessments were continued every six weeks for subjects withdrew from the study for reasons except for observation of radiographically assessed disease progression or receipt of a new anti-tumor therapy, until disease progression was observed. Survival follow-ups were performed every six weeks when the subject developed radiologically assessed disease progression or started to receive a new antitumor therapy.

Each subject's trial includes a screening period, a treatment period and a follow-up period.

After the subjects signed the informed consent form and completed all baseline tests during the screening period, subjects qualified for recruitment were treated with mitoxantrone hydrochloride injections in the order of recruitment. According to the protocols, all subjects received tests specified in the protocols throughout the trial treatment period to assess safety.

2. Study Duration

The study included a screening period of four weeks (28 days), and a treatment period of 8 courses (24 weeks). A follow-up for safety was done four weeks (28 days) after the final dose. Then, PFS follow-ups were done every six weeks, and survival follow-ups were done every six weeks after disease progression. The study duration for each patient was expected to approximately 12 months.

The study plan included recruiting not less than 30 subjects, and the entire duration of the study is expected to be 24 to 36 months.

II. Trial Cohort:

Subjects who met all of the following inclusion criteria and none of the exclusion criteria were recruited in this clinical study.

(1) Inclusion Criteria

Subjects must meet all of the following criteria.

1) voluntarily participating in the study and signing an informed consent form;
2) aged≥18 years for both male and female;
3) histopathologically diagnosed for head and neck squamous cell carcinoma (including nasopharyngeal carcinoma);
4) having recurrent/metastatic head and neck squamous cell carcinoma that underwent at least a first-line therapy failure;
5) bearing at least one measurable lesion that met the definition of RECIST 1.1 at the baseline;
6) having a ECOG score of 0-1;
7) Recovering to grade 1 (except for alopecia, pigmentation, or other toxicity considered not to be a safety risk for the subject in the study) from toxicity due to previous anti-tumor treatment;
8) having the following measurements in the laboratory tests:
   - absolute neutrophil count (ANC)≥$1.5\times10^9$/L (no G-CSF boosting therapy within one week prior to the laboratory tests);
   - hemoglobin (Hb)≥8.0 g/dL (no erythrocyte transfusion therapy or erythropoietin therapy within three months prior to the laboratory tests);
   - platelets≥$75\times10^9$/L, (no transfusion of platelets, thrombopoietin, interleukin-11, or other drugs that elevated platelet level within one week prior to the laboratory tests);
   - creatinine≤1.5×ULN;
   - total bilirubin≤1.5×ULN (≤3×ULN for patients with liver metastasis);
   - alanine aminotransferase (ALT)/aspartate aminotransferase (AST)≤2.5×ULN (≤5×ULN for patients with liver metastasis);
   - albumin≥3.0 g/dL;
   - coagulation with prothrombin time (PT) and international normalized ratio (INR)≤1.5×ULN;
9) being urine or blood HCG negative (except for ones who were at menopause or received hysterectomy) for female subjects, and for those at childbearing age, being able to adopt effective contraception measures (e.g., hormone combination (including estrogen and progestin) in combination with inhibition of ovulation, progestin contraception in combination with inhibition of ovulation, intrauterine device, intrauterine hormone release system, bilateral tubal ligation, vasectomy, or avoidance of sexual behaviour) during the trial and within six months after the final dose; and
10) for male subjects, being able to adopt one of the contraception measures specified in item 9) with their spouses.

(II) Exclusion Criteria:

Subjects meeting any one of the following criteria were excluded from this trial.

1) having severe allergy to mitoxantrone or liposome;
2) having brain or meningeal metastasis;
3) having received allogeneic organ transplantation or allogeneic bone marrow transplantation;
4) having expected survival time of less than three months;
5) having active hepatitis B (HbsAg or HBcAb positive and HBV DNA≥2000 IU/mL), or active hepatitis C (HCV antibody positive and HCV RNA level above the lower limit detectable by the research center), or being HIV antibody positive;
6) having active bacterial infection, fungal infection, viral infection or interstitial pneumonia requiring systemic treatment within one week prior to the first dose;
7) having received any antitumor treatment within four weeks prior to the first dose;
8) having received treatment with a drug in another clinical study within four weeks prior to the first dose;
9) having received major surgery within three months prior to the first dose, or having plans to receive major surgery during the study;
10) having thrombotic or embolic events such as cerebrovascular accidents (including transient ischemic attacks), or pulmonary embolism in the last six months;
11) having other active malignant tumors in the last three years, except for cured local treatable cancer such as basal or squamous cell skin cancer, superficial bladder cancer, or in situ prostate, cervix or breast cancer;
12) having cardiac dysfunction characterized by:
   - long QTc syndrome or QTc interval>480 ms;
   - complete left bundle branch block, or degree II or III atrioventricular block;
   - severe and uncontrolled arrhythmias requiring medical treatment;
   - history of chronic congestive heart failure and NYHA-≥grade 3;
   - cardiac ejection fraction below 50% or below the lower limit detectable by the research center;
   - CTCAE>2 cardiac valvular disease;
   - uncontrolled hypertension (defined as systolic blood pressure>150 mmHg or diastolic blood pressure>90 mmHg with drug management); or
   - myocardial infarction, unstable angina, a history of severe pericardial disease, electrocardiographic evidence of acute ischemic or active conduction system abnormalities occurred within six months prior to screening.
13) having received treatment with doxorubicin or other anthracyclines with cumulative doxorubicin doses in excess of 350 mg/$m^2$ (equivalent dose calculation for anthracyclines: 1 mg doxorubicin=2 mg epirubicin=2 mg daunorubicin=0.5 mg nordoxorubicin=0.45 mg mitoxantrone);
14) being pregnant or lactating;
15) having any serious and/or uncontrollable disease that, in the judgment of the researchers, may affect the patient's participation in the study (including, but not limited to, uncontrolled diabetes, kidney disease requiring dialysis, severe liver diseases, life-threatening autoimmune system diseases and hemorrhagic diseases, drug abuse, and nervous system diseases); and
16) having other factors unfit to participate in the study as judged by the researchers.

(III) Withdrawal/Termination Criteria

Subjects who experienced any of the following events during the study course were discontinued from treatment with the test drug.

1) The subject experienced intolerable toxicity and the researchers believed that the risk in continuing the treatment with study drug outweighs the benefit.
2) Disease progression was observed by imaging assessment.
3) Clinically assessed disease progression was observed, major protocol violation incurred, or the subject had poor compliance, which, in the judgment of the researchers, would not lead to benefit from continued therapy with the test drug.
4) The subject got pregnancy.
5) The subject was dead.
6) The subject meet any of the withdrawal criteria.

All subjects who withdrew from the treatment would still be followed up according to the study protocols, with the exception that subject death is the cause for discontinued treatment, or a subject met any of the following criteria for withdrawal from the study.

Subjects had the right to withdraw from the study at any time for any reason. Subjects would withdraw from the study if any of the following events occurs.

1) The subject is lost from follow-up.
2) The subject withdrew consent or the subject or his/her family member requested the subject to withdraw from the trial.
3) The study terminated.
4) Other III. Research Results Subjects were evaluated for efficacy according to RECIST 1.1 criteria, and subjects were evaluated for all adverse events occurring according to CTCAE 5.0 criteria.

The inventors of the present application anticipate the use of mitoxantrone liposome. The drug has the effects of slow release, targeted action, attenuation, and enhanced efficacy after intravenous infusion into the human body. The dosage is not only higher than that of ordinary injection, but also monotherapy, which can improve the efficacy and reduce the incidence of adverse effects.

A total of 34 subjects were recruited as of Nov. 5, 2021 (the study continued up to now), including 23 nasopharyngeal carcinoma cases and 11 non-nasopharyngeal carcinoma cases (five tongue carcinoma cases, two hypopharyngeal carcinoma cases, two tonsil carcinoma cases, one laryngeal carcinoma case, and one gingival carcinoma case). All subjects were administered mitoxantrone hydrochloride liposome injection at a dose of 20 $mg/m^2$ every three weeks (q3w). Efficacy was assessed after every two courses. 19 subjects received at least one efficacy evaluation (including 18 nasopharyngeal carcinoma subjects and 1 non-nasopharyngeal carcinoma (hypopharyngeal carcinoma) subject). The results of the efficacy analysis showed that the overall ORR was 42.1% (8/19), and the DCR was 78.9% (15/19). The ORR for nasopharyngeal carcinoma was 38.8% (7/18), and the DCR was 77.8% (14/18). One hypopharyngeal carcinoma case was evaluated as PR. No intolerable adverse effects were observed in all subjects.

According to the experimental results up to now, the mitoxantrone hydrochloride liposomal formulation of the present application is expected to provide a second-line treatment for head and neck squamous cell carcinoma, and lay a foundation for the subsequent combination to beat the first-line treatment.

The above description is merely about preferred embodiments, which are by way of example only and do not limit the combination of features essential to practice the present application. The headings provided are not intended to limit the various embodiments in the present application. Terms such as "comprising," "including," and "containing" are not intended to be limiting. Further, unless otherwise indicated, no numerical modification includes the plural, and "or" means "and/or". Unless defined otherwise herein, all technical and scientific terms used herein have the same meaning as commonly understood by one skilled in the art. All publications and patents cited in the present application are incorporated herein by reference. Various modifications and variations of the methods and compositions described herein will be apparent to those skilled in the art without departing from the scope and spirit of the present application. While the present application has been described in reference to specific preferred embodiments, it is to be understood that the claimed inventions should not be unduly limited to these specific embodiments. Indeed, various variations of the described modes for carrying out the present application, which will be apparent to those skilled in the relevant art, are intended to be included within the scope of the appended claims.

The invention claimed is:

1. A method of treating head and neck squamous carcinoma in a subject, comprising administering to the subject a pharmaceutical composition comprising a therapeutically effective amount of mitoxantrone hydrochloride liposome, wherein the head and neck squamous cell carcinoma is recurrent or metastatic head and neck squamous cell carcinoma that has undergone a first line therapy failure.

2. The method of claim 1, wherein the mitoxantrone hydrochloride liposome is the only active ingredient in the pharmaceutical composition.

3. The method of claim 1, wherein the pharmaceutical composition or the mitoxantrone hydrochloride liposome has one or more of the following properties:

(i) the mitoxantrone hydrochloride liposome has a particle size of about 30 to 80 nm;

(ii) the mitoxantrone hydrochloride interacts with a multivalent counter ion in the liposome to form a precipitate;

(iii) a phospholipid bilayer in the mitoxantrone hydrochloride liposome contains a phospholipid having a phase transition temperature (Tm) higher than body temperature, such that the liposome has a phase transition temperature higher than body temperature;

(iv) a phospholipid bilayer in mitoxantrone hydrochloride liposome contains hydrogenated soy phosphatidylcholine, cholesterol and PEG2000 modified distearoylphosphatidylethanolamine (DSPE-PEG2000).

4. The method of claim 3, wherein the mitoxantrone hydrochloride liposome has a particle size of about 40 to 60 nm.

5. The method of claim 3, wherein the multivalent counter ion is sulfate, citrate or phosphate.

6. The method of claim 3, wherein the phospholipid is selected from the group consisting of hydrogenated soy phosphatidylcholine, phosphatidylcholine, hydrogenated egg yolk lecithin, dipalmitate lecithin, distearate lecithin, or any combination thereof.

7. The method of claim 1, wherein a phospholipid bilayer in the mitoxantrone hydrochloride liposome contains hydrogenated soy phosphatidylcholine, cholesterol and PEG2000 modified distearoylphosphatidylethanolamine in a mass ratio of about 3:1:1, the mitoxantrone hydrochloride interacts with a multivalent acid ion in the liposome to form a precipitate, and the mitoxantrone hydrochloride liposome has a particle size of about 60 nm in the pharmaceutical composition.

8. The method of claim 1, wherein the head and neck squamous cell carcinoma is a squamous cell carcinoma occurring in a nasal cavity, sinus, nasopharynx, oropharynx, laryngopharynx, cervical esophagus, thyroid, salivary gland, oral cavity, larynx and/or ear.

9. The method of claim 1, wherein the first line therapy is a combination therapy of cisplatin or carboplatin and 5-FU or paclitaxel, optionally further in combination with cetuximab.

10. The method of claim 1, wherein the pharmaceutical composition is in the form of an injection.

11. The method of claim 10, wherein the pharmaceutical composition is a liquid injection, a powder for injection or a tablet for injection.

12. The method of claim 11, wherein the pharmaceutical composition is a liquid injection and the active ingredient content of the pharmaceutical composition is 0.5 to 5 mg/ml, on the basis of mitoxantrone.

13. The method of claim 11, wherein the pharmaceutical composition is a liquid injection, and the active ingredient content of the pharmaceutical composition is 1 to 2 mg/ml, on the basis of mitoxantrone.

14. The method of claim 1, wherein the pharmaceutical composition is administered by intravenous administration.

15. The method of claim 14, wherein in each intravenous administration, an infusion administration time of the pharmaceutical composition is 30 min to 120 min.

16. The method of claim 14, wherein the pharmaceutical composition is administered is once every four weeks or three weeks.

17. The method of claim 16, wherein the therapeutically effective amount is 8 to 30 $mg/m^2$, on the basis of mitoxantrone.

* * * * *